United States Patent [19]

Kuwada et al.

[11] 3,951,989
[45] Apr. 20, 1976

[54] THIENOPYRIDINE-CARBOXYLIC ACID DERIVATIVES

[75] Inventors: Yutaka Kuwada, Ashiya; Kanji Meguro, Takarazuka; Yoshiaki Sato, Kobe; Takeshi Fugono, Kawanishi, all of Japan

[73] Assignee: Takeda Chemical Industries, Ltd., Osaka, Japan

[22] Filed: July 22, 1974

[21] Appl. No.: 490,704

[30] Foreign Application Priority Data

July 23, 1973  Japan............................... 48-82869
July 23, 1973  Japan............................... 48-82870
Nov. 16, 1973  Japan............................. 48-129352
Nov. 16, 1973  Japan............................. 48-129353

[52] U.S. Cl. .................. 260/294.8 C; 260/294.8 B; 260/330.5; 260/332.2 A; 424/266
[51] Int. Cl.² ...................................... C07D 213/28
[58] Field of Search ............................. 260/294.8 C

[56] References Cited
UNITED STATES PATENTS
3,845,065  10/1974  Shen et al. ................... 260/294.8 C

*Primary Examiner*—Alan L. Rotman
*Attorney, Agent, or Firm*—Wenderoth, Lind and Ponack

[57] ABSTRACT

Novel thienopyridine-carboxylic acid derivatives, which are shown by the general formula

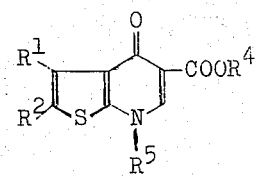

wherein $R^1$ represents hydrogen or a lower alkyl; $R^2$ represents hydrogen, a lower alkyl or a halogen; or $R^1$ and $R^2$, taken together, may represent an alkylene to form a 5- or 6-membered ring with or without alkyl substituents; each of $R^4$ and $R^5$ represents hydrogen or a lower alkyl; and their pharmaceutically acceptable salts obtainable when $R^4$ is hydrogen, which are useful medicines such as chemotherapeutic agents of bacterial infections.

29 Claims, No Drawings

THIENOPYRIDINE-CARBOXYLIC ACID DERIVATIVES

The present invention relates to novel thienopyridine-carboxylic acid derivatives having useful broad antimicrobial spectrum against gram-positive and gram-negative bacteria, which are shown by the general formula (I)

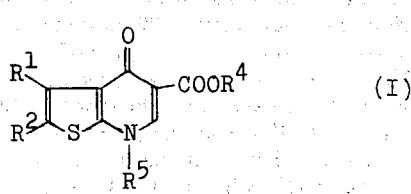

wherein $R^1$ represents hydrogen or a lower alkyl; $R^2$ represents hydrogen, a lower alkyl or a halogen; $R^1$ and $R^2$, taken together, may represent an alkylene to form a 5- or 6-membered ring with or without alkyl substituents; each of $R^4$ and $R^5$ represents hydrogen or a lower alkyl, and their pharmaceutically acceptable salts obtainable when $R^4$ is hydrogen.

The present invention relates also to a process for the production of these thienopyridine-carboxylic acid derivatives.

Hitherto, there have been known many kinds of antimicrobial agents, and some of them have been put into practical use. However, those known antimicbrobial agents are not very satisfactory in the potency of the action, breadth of antimicrobial spectrum, toxicity to human body, etc.

Under these circumstances, present inventors have made extensive studies and succeeded in synthesizing specific new thienopyridine-carboxylic acid derivatives (I) defined above, which have never previously been synthesized.

The present inventors have also found that these compounds have a broad antimicrobial spectrum against gram-positive bacteria e.g., *Staphylococcus aureus, Bacillus subtilis*, etc.; gram-negative bacteria, e.g., *Escherichia coli, Klebsiella pneumoniae, Proteus vulgaris*, etc.; tubercle bacilli and other bacteria, they also show quite a low toxicity and furthermore they have the strong antimicrobial activity either by oral or parenteral administration.

In view of these characteristics, the present compounds can be used as effective medicine for preventing and/or treating bacterial diseases, especially urinary tract infection by means of oral or parenteral administration. The present invention has been accomplished on the basis of these findings.

Thus, the principal object of the present invention is to provide the thienopyridine-carboxylic acid derivatives (I) and their pharmaceutically acceptable salts useful as effective chemotherapeutic agent, and another object of the present invention is to provide a method for the production of these compounds. Other objects will become apparent from the disclosures hereinafter as well as from the appended claims.

In the general formula (I), the lower alkyl group represented by the symbols $R^1$, $R^2$, $R^4$ and $R^5$ respectively may be any of straight- or branched- ones having 1 to 6 carbon atoms or a cyclic alkyl group having 3 to 6 carbon atoms. Typical examples of these alkyl groups may be methyl, ethyl, propyl, isopropyl, n-butyl, isobutyl, sec.-butyl, tert-butyl, pentyl, hexyl, cyclopropylmethyl, cyclopentyl, cyclopentylmethyl and cyclohexyl groups. Among them, for practical purposes, lower alkyl groups having 1 to 3 carbon atoms are preferred. $R^1$ and $R^2$, taken together, may represent an alkylene, for example trimethylene or tetramethylene, to form a 5- or 6-membered ring and on this ring may have substituents which are lower alkyls like those mentioned above in optional positions.

The halogen represented by the symbol $R^2$ may be chlorine, bromine, iodine and fluorine.

In the present invention, the object compounds (I') and (I'') are produced through the reaction steps shown in the following scheme

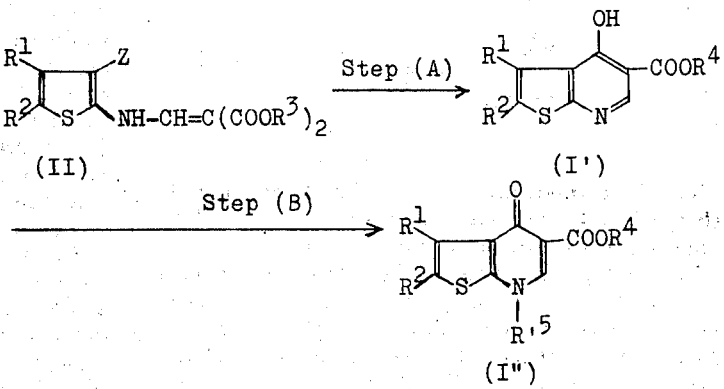

wherein $R^1$, $R^2$ and $R^4$ are as defined above; each of $R^3$ and $R'^5$ represents a lower alkyl; Z represents hydrogen or carboxyl group.

The lower alkyl group represented by the symbol $R^3$ and $R'^5$ have the same meaning as that for $R^1$, $R^2$, $R^4$ and $R^5$.

In Step (A), compound (II) is cyclized by heating to give compound (I') wherein $R^4$ is the same lower alkyl as represented by $R^3$ followed by, if necessary, hydrolysis to give compound (I') wherein $R^4$ is hydrogen.

The cyclization is carried out by heating in the absence of a solvent or, alternatively, in a suitable heat-transfer solvent such as benzene, toluene, xylene, tetralin, nitrobenzene, dichlorobenzene, diphenyl ether or biphenyl, or a mixture of such solvents. The reaction temperature is ordinarily within the range of 150°C to 250°C and, preferably, between 180°C to 230°C. If a catalyst capable of promoting the cyclization is added, the reaction may be conducted at a lower temperature. Among the catalysts suited for the purpose, there may be mentioned polyphosphate ester, polyphosphoric acid, phosphorus pentoxide, etc. With such a catalyst, the temperature range of, ordinarily, 60°C to 170°C and, preferably, 75°C to 150°C is employed.

When, in this reaction, use is made of starting compound (II) wherein Z means a carboxyl group, it undergoes a decarboxylation followed by cyclization to give compound (I').

The compound (I') wherein $R^4$ is the same lower alkyl group as $R^3$ is produced by this reaction and it can be isolated in optional purity by procedures which are conventional per se, for example by recrystallization, chromatography, etc. If necessary, the ester can be hydrolyzed to compound (I') wherein $R^4$ is hydrogen. This hydrolysis can be accomplished by hydrolytic procedures which are conventional per se, that is to say under whichever of acid and alkaline conditions. Ordinarily, the hydrolysis is conducted with a mineral acid (e.g. hydrochloric acid, hydrobromic acid or sulfuric acid) or an alkali hydroxide (e.g. sodium hydroxide or potassium hydroxide) in a solvent which may, for example, be water, methanol, ethanol, acetone or dioxane. (When the substrate compound is only sparingly soluble, the reaction may be performed in suspension). The resulting compound in which $R^4$ is hydrogen can be isolated in optional purity by procedures conventional per se, for example, by recrystallization, chromatography, etc.

These compounds (I') may be represented by a tautomeric structure of the general formula (I'''):

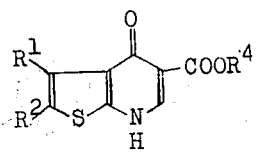

(I''')

Namely, compounds (I'), (I''') and compound (I) wherein $R^5$ is hydrogen respectively denote one and the same compound, whichever formula may be given.

Then, in Step (B), there can be obtained the N-alkyl compounds (I''). The alkylation is carried out using one of the conventional alkylating agents which include, among others, alkyl halides, dialkyl sulfates, alkyl sulfonates, etc. Ordinarily this reaction is conducted in the presence of an alkali and in a solvent which is inert to the reaction. The solvent [when (I') is insoluble, the reaction may be performed in suspension] includes water, methanol, ethanol, acetone, dioxane, benzene, dimethylformamide, dimethylsulfoxide, etc. as well as mixtures of such solvents. Advantageous examples of the alkali which may be used are alkali hydroxide (e.g. sodium hydroxide, potassium hydroxide, etc.) and alkali carbonate (e.g. sodium carbonate, potassium carbonate, etc.). If necessary, alkali alcoholate (e.g. sodium methylate, sodium ethylate, potassium methylate, potassium ethylate, etc.), alkali hydride (e.g. sodium hydride), sodium amide, potassium amide, etc. may be used together with an anhydrous solvent. Ordinarily the reaction proceeds even at room temperature, but, to control the reaction rate, the reaction system may be cooled to a temperature below room temperature or heated up to the boiling point of the solvent used. The ratio of the alkylating agent and that of the alkali are 1 to 20 moles and preferrably 1 to 10 moles per mole of (I').

Generally speaking, the above reaction gives compound (I'') in which $R^4$ is hydrogen from compound (I') in which $R^4$ is hydrogen, or compound (I'') in which $R^4$ is a lower alkyl group from compound (I') in which $R^4$ is a lower alkyl group. However, when a strong alkali such as alkali hydroxide is used and, particularly, heat is applied, even compound (I') wherein $R^4$ is a lower alkyl group is at times hydrolyzed to give compound (I'') in which $R^4$ is hydrogen.

On the other hand, when an alcoholate, sodium hydride or sodium amide, for instance, is used together with an anhydrous solvent, even when $R^4$ in compound (I') is hydrogen, the N-alkylation is at times accompanied by the alkylation of the carboxyl function to give compound (I'') wherein $R^4$ is a lower alkyl group. Therefore, when it is particularly desired to obtain compound (I'') wherein $R^4$ is hydrogen, there are alternative procedures, one of which comprises the use of a strong alkali like those mentioned above so as to cause the N-alkylation and the hydrolysis of the ester to take place simultaneously and the other procedure being a stepwise one in which N-alkylation is first conducted and, then, the ester is hydrolyzed, whereby compound (I'') in which $R^4$ is hydrogen is obtained even using compound (I') in which $R^4$ is a lower alkyl group.

Conversely when it is particularly desired to obtain compound (I'') in which $R^4$ is a lower alkyl group, the desired product in which $R^4$ is a lower alkyl group can be produced, even if use is made of compound (I') in which $R^4$ is hydrogen, by conducting N-alkylation and O-alkylation (esterification) under anhydrous conditions as mentioned above.

When $R^4$ in compound (I'') obtained in Step (B) is hydrogen, the compound can be esterified by a procedure known per se to compound (I'') in which $R^4$ is a lower alkyl group. The advantageous esterification procedures are those in which compound (I'') wherein $R^4$ is hydrogen or a reactive derivative at the carboxyl function of said compound is reacted with alcohols, alkyl halides, alkyl sulfonates, dialkyl sulfates, diazoalkanes (e.g. diazomethane, diazoethane) and the like.

Examples of the reactive derivatives at the carboxyl function of said compound include the corresponding carboxylic acid anhydride, carboxylic acid halides (e.g. bromide, chloride), carboxylic acid metal salts of, for example, sodium, potassium, silver. The alcohols may for example be methanol, ethanol, n-propanol, iso-propanol, n-butanol, iso-butanol, tert-butanol, etc. The alkyl halide may for instance be methyl iodide, ethyl iodide or n- or iso-propyl-bromide and -iodide.

When $R^4$ in compound (I'') obtained in Step (B) is a lower alkyl group, it can be converted to compound (I'') wherein $R^4$ is hydrogen by a hydrolysis which is conventional per se.

The hydrolysis can be accomplished by that conducted on compound (I') mentioned above or a procedure analogous thereto.

The compound (I'') produced by the foregoing procedures can be isolated in optional purity by separation and purification procedures which are conventional per se, e.g. recrystallization, chromatography, etc.

In the case of compound (I') and (I'') in which $R^4$ is hydrogen, the acid hydrogen of the carboxylic acid function can be made into an alkali metal salt, alkaline earth metal salt, ammonium salt or the like by means of an alkali hydroxide, alkali carbonate, alkali hydrogen carbonate, ammonia, organic amine or the like. Examples of said salts include the corresponding salts of sodium, potassium, calcium, magnesium, aluminum, ammonium, methylamine, dimethylamine, trimethylamine, ethylamine, diethylamine, triethylamine, ethanolamine, diethanolamine, etc.

The compounds (I') (I'') and their pharmaceutically acceptable salts obtainable when $R^4$ is hydrogen of this invention possess a broad antimicrobial spectrum against gram-positive and gram-negative bacteria, tubercle bacilli and other bacteria, and they are useful compounds which can be widely employed as chemotherapeutic agents of bacterial infections.

Any of these compounds can be administered, either as it is or in combination with a suitable pharmaceutically acceptable vehicle or excipient if desired, in such optional dosage forms as tablets, powders, granules, injections, syrups, etc. While the dosage depends upon the subject of administration (e.g. man or other mammals), symptoms, the properties of the individual compound (I') and (I''), daily oral dose for adult humans may be selected from the range of about 100 mg. to 10 g.

By the method of this invention there can be produced the following compounds.

4-Hydroxythieno[2,3-b]pyridine-5-carboxylic acid, and its methyl or ethyl ester

4-Hydroxy-2-methylthieno[2,3-b]pyridine-5-carboxylic acid, and its methyl or ethyl ester 2-Ethyl-4-hydroxythieno[2,3-b]pyridine-5-carboxylic acid, and its methyl or ethyl ester 4-Hydroxy-2-propylthieno[2,3-b]pyridine-5-carboxylic acid, and its methyl or ethyl ester 4-Hydroxy-2-isopropylthieno[2,3-b]pyridine-5-carboxylic acid, and its methyl or ethyl ester 4-Hydroxy-3-methylthieno[2,3-b]pyridine-5-carboxylic acid, and its methyl or ethyl ester 3-Ethyl-4-hydroxythieno[2,3-b]pyridine-5-carboxylic acid, and its methyl or ethyl ester 4-Hydroxy-3-propylthieno[2,3-b]pyridine-5-carboxylic acid, and its methyl or ethyl ester 2,3-Dimethyl-4-hydroxythieno[2,3-b]pyridine-5-carboxylic acid, and its methyl or ethyl ester 3-Ethyl-4-hydroxy-2-methylthieno[2,3-b]pyridine-5-carboxylic acid, and its methyl or ethyl ester 6,7-Dihydro-4-hydroxy-5H-cyclopenta[4,5]-thieno[2,3-b]-pyridine-3-carboxylic acid, and its methyl or ethyl ester 4-Hydroxy-5,6,7,8-tetrahydro-[1]benzothieno[2,3-b]pyridine-3-carboxylic acid, and its methyl or ethyl ester 4-Hydroxy-5-methyl-5,6,7,8-tetrahydro-[1]benzothieno[2,3-b]-pyridine-3-carboxylic acid, and its methyl or ethyl ester 2-Chloro-4-hydroxythieno[2,3-b]pyridine-5-carboxylic acid, and its methyl or ethyl ester 2-Chloro-4-hydroxy-3-methylthieno[2,3-b]pyridine-5-carboxylic acid, and its methyl or ethyl ester 2-Bromo-4-hydroxythieno[2,3-b]pyridine-5-carboxylic acid, and its methyl or ethyl ester 2-Bromo-4-hydroxy-3-methylthieno[2,3-b]pyridine-5-carboxylic acid, and its methyl or ethyl ester 2-Bromo-3-ethyl-4-hydroxythieno[2,3-b pyridine-5-carboxylic acid, and its methyl or ethyl ester 2-Bromo-4-hydroxy-3-isopropylthieno[2,3-b]pyridine-5-carboxylic acid, and its methyl or ethyl ester 2-Bromo-3-butyl-4-hydroxythieno[2,3-b]pyridine-5-carboxylic acid, and its methyl or ethyl ester 4-Hydroxy-2-iodothieno[2,3-b]pyridine-5-carboxylic acid, and its methyl or ethyl ester 4-Hydroxy-2-iodo-3-methylthieno[2,3-b pyridine-5-carboxylic acid, and its methyl or ethyl ester By alkylating the 4-hydroxythieno[2,3-b]pyridine-5-carboxylic acids or their carboxylic esters, the following compouns can be produced, for instance.

4,7-Dihydro-7-methyl-4-oxothieno[2,3-b]pyridine-5-carboxylic acid and its methyl or ethyl ester 7-Ethyl-4,7-dihydro-4-oxothieno[2,3-b]pyridine-5-carboxylic acid and its methyl or ethyl ester 4,7-Dihydro-4-oxo-7-propylthiono[2,3-b]pyridine-5-carboxylic acid and its methyl or ethyl ester 4,7-Dihydro-7-isopropyl-4-oxothieno[2,3-b]pyridine-5-carboxylic acid and its methyl or ethyl ester 7-Butyl-4,7-dihydro-4-oxothieno[2,3-b]pyridine-5-carboxylic acid and its methyl or ethyl ester 4,7-Dihydro-7-isobutyl-4-oxothieno [2,3-b]pyridine-5-carboxylic acid and its methyl or ethyl ester 7-tert-Butyl-4,7-dihydro-4-oxothieno[2,3-b]pyridine-5-carboxylic acid and its methyl or ethyl ester 4,7-Dihydro-7-pentyl-4-oxothieno[2,3-b]pyridine-5-carboxylic acid and its methyl or ethyl ester 7-Hexyl-4,7-dihydro-4-oxothieno[2,3-b]pyridine-5-carboxylic acid and its methyl or ethyl ester The 7-methyl, 7-ethyl, 7-propyl, 7-isopropyl, 7-butyl, 7-isobutyl, 7-tert-butyl, 7-pentyl and 7-hexyl derivatives of 4,7-dihydro-2-methyl-4-oxothieno[2,3-b]pyridine-5-carboxylic acid and its methyl or ethyl ester The 7-methyl, 7-ethyl, 7-propyl, 7-isopropyl, 7-butyl, 7-pentyl and 7-hexyl derivatives of 2-ethyl-4,7-dihydro-4-oxothieno[2,3-b]pyridine-5-carboxylic acid and its methyl or ethyl ester The 7-methyl, 7-ethyl, 7-propyl and 7-butyl derivatives of 4,7-dihydro-4-oxo-2-propylthieno[2,3-b]pyridine-5-carboxylic acid and its methyl or ethyl ester The 7-methyl, 7-ethyl, 7-propyl and 7-butyl derivatives of 4,7-dihydro-2-isopropyl-4-oxothieno[2,3-b]pyridine-5-carboxylic acid and its methyl or ethyl ester The 7-methyl, 7-ethyl, 7-propyl and 7-butyl derivatives of 4,7-dihydro-3-methyl-4-oxothieno[2,3-b]pyridine-5-carboxylic acid and its methyl or ethyl ester The 7-methyl, 7-ethyl, 7-propyl and 7-butyl derivatives of 3-ethyl-4,7-dihydro-4-oxothieno[2,3-b]pyridine-5-carboxylic acid and its methyl or ethyl ester The 7-methyl, 7-ethyl, 7-propyl and 7-butyl derivatives of 4,7-dihydro-4-oxo-3-propylthieno[2,3-b]pyridine-5-carboxylic acid and its methyl or ethyl ester The 7-methyl, 7-ethyl, 7-propyl and 7-butyl derivatives of 4,7-dihydro-2,3-dimethyl-4-oxothieno[2,3-b]pyridine-5-carboxylic acid and its methyl or ethyl ester The 7-methyl, 7-ethyl, 7-propyl and 7-butyl derivatives of 3-ethyl-4,7-dihydro-2-methyl-4-oxothieno[2,3-b]pyridine-5-carboxylic acid and its methyl or ethyl ester The 1-methyl, 1-ethyl, 1-propyl and 1-butyl derivatives of 1,4,6,7-tetrahydro-4-oxo-5H-cyclopenta[4,5]-thieno[2,3-b]-pyridine-3-carboxylic acid and its methyl or ethyl ester The 1-methyl, 1-ethyl, 1-propyl, 1-isopropyl, 1-butyl, 1-pentyl and 1-hexyl derivatives of 4-oxo-1,4,5,6,7,8-hexahydro-[1]benzothieno [2,3-b]pyridine-3-carboxylic acid and its methyl or ethyl ester The 1-methyl, 1-ethyl, 1-propyl and 1-butyl derivatives of 5-methyl-4-oxo-1,4,5,6,7,8-hexahydro-[1]benzothieno[2,3-b]-pyridine-3-carboxylic acid and its methyl or ethyl ester 2-Chloro-4,7-dihydro-7-methyl-4-oxothieno[2,3-b]pyridine-5-carboxylic acid, and its methyl or ethyl ester
2-Chloro-7-ethyl-4,7-dihydro-4-oxothieno[2,3-b]pyridine-5-carboxylic acid, and its methyl or ethyl ester
2-Chloro-4,7-dihydro-4-oxo-7-propylthieno[2,3-b]pyridine-5-carboxylic acid and its methyl or ethyl ester
2-Chloro-4,7-dihydro-7-isopropyl-4-oxothieno[2,3-b]pyridine-5-carboxylic acid, and its methyl or ethyl ester
2-Chloro-4,7-dihydro-3,7-dimethyl-4-oxothieno[2,3-b]pyridine-5-carboxylic acid, and its methyl or ethyl ester
2-Chloro-7-ethyl-4,7-dihydro-3-methyl-4-oxothieno[2,3-b]-pyridine-5-carboxylic acid, and its methyl or ethyl ester
2-Bromo-4,7-dihydro-7-methyl-4-oxothieno[2,3-b]pyridine-5-carboxylic acid, and its methyl or ethyl ester
2-Bromo-7-ethyl-4,7-dihydro-4-oxothieno[2,3-b]pyridine-5-carboxylic acid, and its methyl or ethyl ester
2-Bromo-4,7-dihydro-4-oxo-7-propylthieno[2,3-b]pyridine-5-carboxylic acid, and its methyl or ethyl ester
2-Bromo-4,7-dihydro-7-isopropyl-4-oxothieno[2,3-b]pyridine-5-carboxylic acid, and its methyl or ethyl ester
2-Bromo-7-butyl-4,7-dihydro-4-oxothieno[2,3-b]pyridine-5-carboxylic acid, and its methyl or ethyl ester
2-Bromo-7-cyclopropylmethyl-4,7-dihydro-4-oxothieno[2,3-b]-pyridine-5-carboxylic acid, and its methyl or ethyl ester
2-Bromo-4,7-dihydro-3,7-dimethyl-4-oxothieno[2,3-b]pyridine-5-carboxylic acid, and its methyl or ethyl ester
2-Bromo-7-ethyl-4,7-dihydro-3-methyl-4-oxothieno[2,3-b]-pyridine-5-carboxylic acid, and its methyl or ethyl ester
2-Bromo-4,7-dihydro-3-methyl-4-oxo-7-propylthieno[2,3-b]-pyridine-5-carboxylic acid, and its methyl or ethyl ester
2-Bromo-3,7-diethyl-4,7-dihydro-4-oxothieno[2,3-b]pyridine-5-carboxylic acid, and its methyl or ethyl ester
2-Bromo-4,7-dihydro-7-methyl-3-isopropyl-4-oxothieno[2,3-b]-pyridine-5-carboxylic acid, and its methyl or ethyl ester
2-Bromo-7-ethyl-4,7-dihydro-3-isopropyl-4-oxothieno[2,3-b]-pyridine-5-carboxylic acid, and its methyl or ethyl ester
2-Bromo-3-butyl-7-ethyl-4,7-dihydro-4-oxothieno[2,3-b]-pyridine-5-carboxylic acid, and its methyl or ethyl ester
4,7-Dihydro-2-iodo-7-methyl-4-oxothieno[2,3-b]pyridine-5-carboxylic acid, and its methyl or ethyl ester
7-Ethyl-4,7-dihydro-2-iodo-4-oxothieno[2,3-b]pyridine-5-carboxylic acid, and its methyl or ethyl ester
4,7-Dihydro-2-iodo-4-oxo-7-propylthieno[2,3-b]pyridine-5-carboxylic acid, and its methyl or ethyl ester
4,7-Dihydro-3,7-dimethyl-2-iodo-4-oxothieno[2,3-b]pyridine-5-carboxylic acid, and its methyl or ethyl ester
7-Ethyl-4,7-dihydro-2-iodo-3-methyl-4-oxothieno[2,3-b]-pyridine-5-carboxylic acid, and its methyl or ethyl ester The starting material (II) wherein $R^2$ is hydrogen or a lower alkyl group for this invention can be produced, for example, by the procedure shown by the following scheme.

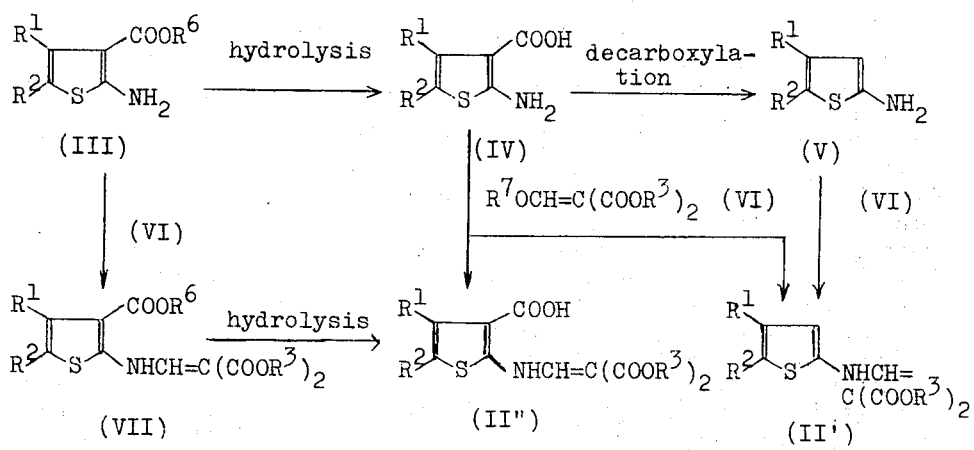

Note:
(II') means a compound (II) wherein Z is hydrogen.
(II'') means a compound (II) wherein Z is carboxyl group. (wherein $R^1$ and $R^3$ are as defined above; $R^6$ and $R^7$ respectively, represent a lower alkyl group like those mentioned for $R^1$ through $R^5$ and $R'^5$)

The compound represented by general formula (III) can be produced, for example, by the process described in Chemische Berichte 98, 3571(1965) or a process similar thereto. Hydrolysis of compound (III) gives compound (IV) which, when decarboxylated, yields compound (V). These hydrolysis and decarboxylation can be carried out by the procedures described in Zeitschrift fuer Chemie 7, 186(1967) or those analogous thereto. Such a compound (IV) or (V), when reacted with an alkoxymethylenemalonate of general formula (VI), gives a starting compound (II) for this invention. This reaction is effected by heating compound (IV) or (V) with compound (VI). This reaction is conducted ordinarily in the absence of a solvent and at 50°C to 150°C and, preferably, at 90°C to 130°C, although use may be made of a solvent inert to the reaction which may for example be a hydrocarbon such as benzene, toluene or xylene.

The ratio of compound (VI) is ordinarily 1 to 2 moles and, preferably, about 1 to 1.3 moles per mole of (IV) or (V). By this reaction is obtained compound (II') corresponding to (II) wherein Z is hydrogen from (V). From (IV), there is usually obtained a mixture of starting material (II'') corresponding to (II) wherein Z is carboxyl and its decarboxylated product (II'). (II') and (II'') can be easily separated by such a procedure as recrystallization or chromnatography. Since the method of this invention enables compound (I') to be produced from whichever of (II') and (II''), the mixture of (II') and (II'') can be used as it is as the starting material. Compound (II'') can also be prepared by the alternative route, i.e. reaction of (III) with (VI) to give compound (VII) followed by alkaline hydrolysis.

The starting material (II) wherein $R^2$ is halogen for this invention can be produced, for example, by the procedure shown by the following scheme.

tively. This halogenation is performed using a conventional halogenating agent such as halogen, sulfuryl halide (sulfuryl chloride, sulfuryl bromide, etc.), N-halogenoacetamide (e.g. N-chloro- or N-bromoacetamide), N-halogenosuccinimide (e.g. N-chloro- or N-bromosuccinimide) or the like. The ratio of said halogenating agent is 1 to 5 moles and, preferably, about 1 to 1.5 moles per mole of (XI) or (XII). The reaction is ordinarily conducted in the presence of a solvent and around a room temperature but for the purpose of controlling the reaction rate, the temperature may be increased or decreased within the range of about

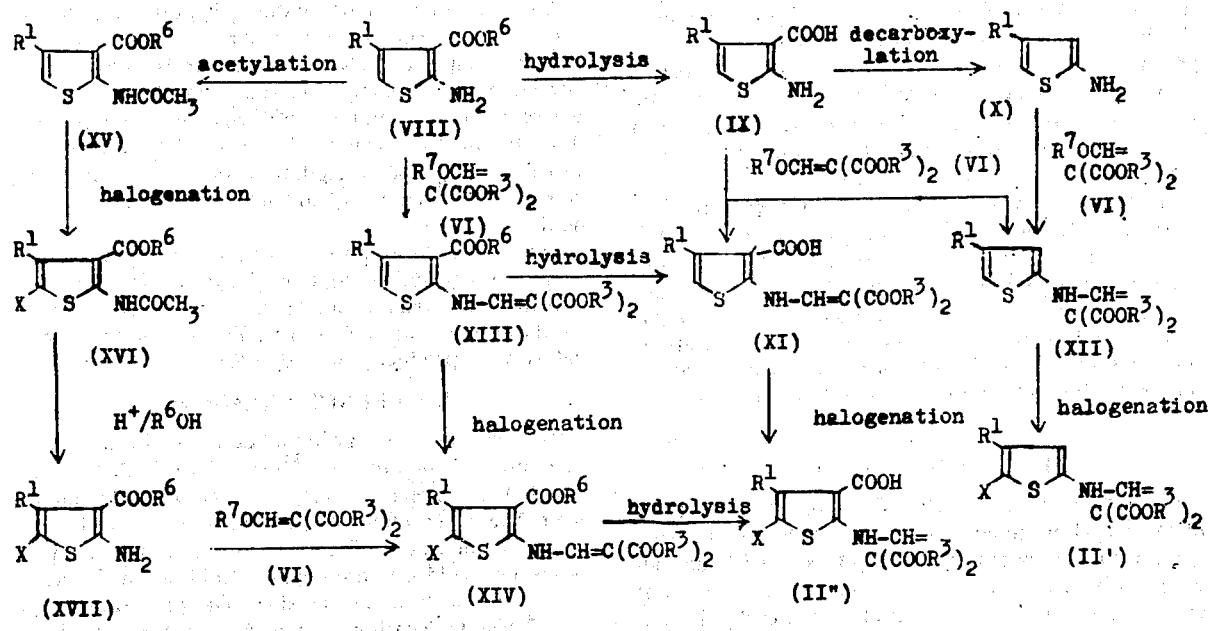

(wherein $R^1$, $R^3$, $R^6$, and $R^7$ are each as defined above; X represents a halogen mentioned for $R^2$)

Compounds (VIII), (IX) and (X) can be prepared by analogous methods to those mentioned in compounds (III), (IV) and (V).

The compound (IX) or (X), when reacted with an alkoxymethylene malonate (VI), gives compound (XI) or (XII). This reaction consists in heating compound (IX) or (X) together with compound (VI). This reaction is carried out ordinarily in the absence of a solvent at 50°C to 150°C and, preferably, 90°C to 130°C but, if neccesary, use may be made of a suitable solvent that is inert to the reaction, such as hydrocarbon, e.g. benzene, toluene or xylene. The ratio of compound (VI) is usually 1 to 2 moles and preferably about 1 to 1.3 moles to each mole of (IX) or (X).

From compound (IX), this reaction gives rise to a mixture of (XI) and its decarboxylation product (XII). These compounds (XI) and (XII) can be easily separated from each other by separation procedures such as recrystallization, chromatography, etc.

The resultant compound (XI) aND (XII), upon halogenation, yield compound (II'') corresponding to (II) wherein Z is a carboxyl group and compound (II') corrresponding to (II) wherein Z is hydrogen, respec- −20°C to about 100°C. Ordinarily the solvent may be carbon tetrachloride, chloroform, dichloromethane, ethyl ether, dioxane or acetic acid or a mixture of such solvents. To the reaction system may be added an acid acceptor such as pyridine, triethylamine, sodium carbonate, potassium carbonate, sodium hydrogen carbonate, potassium hydrogen carbonate, sodium acetate, potassium acetate, mercuric oxide, mercuric acetate or the like, to accept the hydrogen halide produced and to allow the reaction to proceed smoothly.

Further, compound (II'') wherein Z is a carboxyl group can also be produced by reacting (VIII) with (VI) to produce compound (XIII) and, then, either hydrolyzing it followed by halogenation [(XIII) → (XI) → (II'')] or halogenating it followed by hydrolysis [(XIII) → (XIV) → (II'')]. Compound (II'') can also be produced by the process which consists of acetylating compound (VIII) to compound (XV), halogenating (XV) to compound (XVI), subjecting the resultant compound (XVI) to solvolysis to remove the acetyl group, then reacting the compound (XVII) with (VI) in a manner similar to that described above to obtain (XIV) and finally hydrolyzing the compound (XIV) [(VIII)→(XV)→(XVI)→(XVII)→(XIV)→(II'')].

Hydrolysis of compound (XIII) or (XIV) is effected by means of an alkali as it is the case with the hydrolysis of compound (VIII). Thus, preferably the hydrolysis is carried out using a methanolic or ethanolic sodium hydroxide or potassium hydroxide within the temperature range of room temperature to the boiling point of the solvent used. In this reaction, the sodium or potassium salt of (XIII) or (XIV) usually separates out from the reaction system. The salt can easily be converted to free (XI) or (II'') by neutralizing with an acid (e.g. acetic acid, hydrochloric acid or sulfuric acid). The halogenation of (XIII) or (XV) can be conducted under conditions similar to those mentioned in the halogenation of (XI) or (XII). The acetylation of (VIII) can be carried out by the procedure described in Chemische Berichte 98, 3571 (1965) or by a procedure analogous thereto, and the solvolysis of compound (XVI) is conducted in methanol or ethanol and in the presence of an acid catalyst (e.g. hydrogen chloride, hydrogen bromide, sulfuric acid, p-toluenesulfonic acid, methanesulfonic acid, boron trifluoride, etc.) within the temperature range of room temperature to the boiling point of the solvent used.

The following Examples are intended merely to illustrate presently preferred embodiments of the present invention and not to restrict the scope of this invention.

The following Reference Examples and Examples are given, wherein the terms "part(s)" means "weight part(s)" unless otherwise specified, and the relationship between "part(s)" and "part(s) by volume" corresponds to that between gram(s) and milliliter(s).

REFERENCE EXAMPLE 1

A mixture of 15.7 parts of 2-amino-5-methylthiophene-3-carboxylic acid and 23 parts of diethyl ethoxymethylenemalonate is heated at 110°C for 1 hour and, after cooling, isopropyl ether is added. The resultant crystals are recovered by filtration, whereby 2-(2,2-bisethoxycarbonyl)vinylamino-5-methylthiophene-3-carboxylic acid is obtained as crystals. Recrystallization from ether gives light-yellowish needles melting at 180°–185°C.

Elemental analysis, $C_{14}H_{17}NO_6S$.

Calcd: C, 51.36; H, 5.23; N, 4.27. Found: C, 51.12; H, 5.14; N, 4.32.

The filtrate after separation of the above crystals is run onto a column of 100 parts silica gel and elution is carried out with isopropyl ether. The eluate is concentrated and the oily residue is dissolved in a small amount of ethanol and cooled in a dry ice-acetone bath. The resultant crystals are recovered by filtration and washed with cold ethanol, whereupon diethyl (5-methylthienyl)aminomethylenemalonate is obtained as crystals. Light-yellowish needles, melting point: 54°–55.5°C.

Elemental analysis, $C_{13}H_{17}NO_4S$. Calcd: C, 55.10; H, 6.05; N, 4.94. Found: C, 55.15; H, 5.98; N, 5.09.

REFERENCE EXAMPLE 2

Amino-5-methylthiophene is reacted with diethyl ethoxymethylenemalonate by a procedure similar to that described in Reference Example 1, whereupon diethyl (5-methylthienyl)aminomethylenemalonate is obtained as crystals. Light-yellowish needles, melting point: 54°–55.5°C.

This product is identical with the product obtained in Reference Example 1.

REFERENCE EXAMPLE 3

A mixture of 3.7 parts of ethyl 2-amino-5-methylthiophene-3-carboxylate and 4.4 parts of diethyl ethoxymethylenemalonate is heated at 110°C for 1.5 hour. After cooling ethanol is added and the crystals are collected by filtration, whereby diethyl (3-ethoxycarbonyl-5-methylthienyl)aminomethylenemalonate is obtained as crystals. Recrystallization from ethanol gives pale yellow needles melting at 67°–68°C.

Elemental analysis, $C_{16}H_{21}NO_6S$. Calcd: C, 54.07; H, 5.96; N, 3.94. Found: C, 54.07; H, 6.10; N, 3.77.

REFERENCE EXAMPLE 4

A mixture of 3.55 parts of diethyl (3-ethoxycarbonyl-5-methylthienyl)aminomethylenemalonate and 100 parts by volume of 10 % ethanolic potassium hydroxide is heated on a boiling water bath for a few minutes, whereby the potassium salt of the product precipitates. After the mixture is allowed to stand at room temperature for 6 hours the precipitate is collected by filtration, washed with ethanol and added to diluted hydrochloric acid.

This procedure gives 2-(2,2-bisethoxycarbonyl)vinylamino-5-methylthiophene-3-carboxylic acid as crystals. Recrystallization from ethanol-ether gives needles melting at 180°–185°C. This product is identical with the product obtained in Reference Example 1.

REFERENCE EXAMPLE 5

By a procedure similar to that described in Reference Example 1, a mixture of 21.6 parts of diethyl ethoxymethylenemalonate and 19.7 parts of 2-amino-4,5,6,7-tetrahydrobenzo[b]thiophene-3-carboxylic acid is heated at 110°–120°C for 1.5 hour and then, n-hexane is added to the mixture, followed by filtration to recover the resultant crystals. The procedure gives 2-(2,2-bisethoxycarbonyl)vinylamino-4,5,6,7-tetrahydrobenzo[b]thiophene-3-carboxylic acid as crystals. Recrystallization from ethanol gives yellow crystals, melting a 164°–165°C.

The n-hexane solution after filtration of the above crystals is concentrated and run onto a column of silica gel. Then, elution is performed with isopropyl ether, whereupon diethyl (4,5,6,7-tetrahydrobenzo[b]thienyl)aminomethylenemalonate is obtained as an oily product. Infrared absorption spectrum $(cm^{-1})$ 3250, 1720, 1690, 1650.

REFERENCE EXAMPLE 6

To 1.97 part of 2-amino-4,5,6,7-tetrahydrobenzo[b]thiophene-3-carboxylic acid are added 10 parts by volume of isopropanol and 1 g. of oxalic acid and the mixture is warmed at 35°C for 1 hour. The crystals are collected by filtration, washed with isopropanol and dried, whereupon 2-amino-4,5,6,7-tetrahydrobenzo[b]thiophene oxalate are obtained as crystals, melting point: about 95°C (decomposition). A solution of this compound in 50 parts by volume of water is made alkaline by the addition of concentrated aqueous ammonia and the mixture is extracted with ether. The ethereal extract is dried over $Na_2SO_4$ and the solvent is distilled off. To the residue is added 1.8 parts of diethyl ethoxymethylenemalonate and the mixture is heated at 110°C for 20 minutes, and then dissolved in isopropyl ether. The solution is run onto a column of silica gel and elution is carried out with isopropyl ether. The above procedure gives diethyl (4,5,6,7-tetrahydrobenzo[b]thienyl)aminomethylenemalonate as an oil. The infrared absorption spectrum of this product is in agreement with that of the compound obtained in Reference Example 3.

REFERENCE EXAMPLE 7

By a procedure analogous to that described in Reference Example 1, 34 parts of 2-amino-5-ethylthiophene-3-carboxylic acid is reacted with 42 parts of diethyl ethoxymethylenemalonate to obtain 2-(2,2-bisethoxycarbonyl)vinylamino-5-ethylthiophene-3-carboxylic acid as crystals. Recrystallization from ethanol gives light-yellowish crystals melting at 160°–161°C.

REFERENCE EXAMPLE 8

A mixture of 15 parts of ethyl 2-amino-4,5-dimethylthiophene-3-carboxylate and 75 parts by volume of 2N solution of sodium hydroxide in 50 % aqueous ethanol is refluxed for 2.5 hours. After cooling the solution is diluted with 75 parts by volume of water and neutralized with acetic acid under cooling with ice. The resulting precipitate is collected by filtration to give 2-amino-4,5-dimethylthiophene-3-carboxylic acid as crystals. Recrystallization from chloroform with charcoal gives colorless needles melting at 136°–138°C (decomposition).

REFERENCE EXAMPLE 9

Reaction of 2-amino-4,5-dimethylthiophene-3-carboxylic acid with diethyl ethoxymethylenemalonate in a manner similar to that described in Reference Example 1 gives 2-(2,2-bisethoxycarbonyl)-vinylamino-4,5dimethylthiophene-3-carboxylic acid as crystals. Recrystallization from ethyl acetate gives yellowish crystals melting at 182°–183°C (decomposition).

The mother liquor after filtration of the above crystals is concentrated and purified by a silica gel column chromatography to give diethyl (4,5-dimethylthienyl)aminomethylenemalonate as crystals. Recrystallization from aqueous methanol gives prisms melting at 85°–86°C.

REFERENCE EXAMPLE 10

A mixture of 31.4 parts of methyl 2-aminothiophene-3-carboxylate and 43.2 parts of diethyl ethoxymethylenemalonate is heated on an oil bath at 110°–115°C for 1.5 hours, whereupon diethyl (3-methoxycarbonylthienyl)aminomethylenemalonate is obtained as crystals. Recrystallization from ethanol gives light-yellowish needles melting at 137°–138°C.

Elemental analysis, $C_{14}H_{17}NO_6S$. Calcd.: C, 51.36; H, 5.23; N, 4.28. Found: C, 51.30; H, 5.36; N, 4.17.

REFERENCE EXAMPLE 11

To 300 parts by volume of a 3N methanolic solution of potassium hydroxide is added 16.4 parts of diethyl (3-methoxycarbonylthienyl)aminomethylenemalonate and the mixture is stirred on a boiling water bath for a few minutes, whereupon the starting material is dissolved and the potassium salt of the product separates out. After standing at room temperature for 2 hours, the crystals are collected by filtration and neutralized with dilute hydrochloric acid, whereby 2-(2,2-bisethoxycarbonyl)vinylaminothiophene-3-carboxylic acid is obtained as crystals. Recrystallization from ethanol gives light-yellowish needles melting at 167°–169°C.

Elemental analysis, $C_{13}H_{15}NO_6S$. Calcd.: C, 49.83; H, 4.83; N, 4.47. Found: C, 49.72; H, 4.92; N, 4.22.

REFERENCE EXAMPLE 12

To a solution of 9.4 parts of 2-(2,2-bisethoxycarbonyl)vinylaminothiophene-3-carboxylic acid in a mixture of 90 parts by volume of chloroform and 12 parts by volume of pyridine, 1.6 parts by volume of bromine is added dropwise with stirring. After stirring at room temperature for 40 minutes, the solvent is distilled off under reduced pressure.

After the addition of water to the residue, the mixture is made acidic by the addition of dilute hydrochloric acid, whereupon 2-(2,2-bisethoxycarbonyl)-vinylamino-5-bromothiophene-3-carboxylic acid is obtained as crystals. Recrystallization from methanol gives light-yellowish needles melting at 191°–193°C.

Elemental analysis, $C_{13}H_{14}BrNO_6S$. Calcd.: C, 39.81; H, 3.60; N, 3.57. Found: C, 39.47; H, 3.21; N, 3.27.

REFERENCE EXAMPLE 13

To a solution of 3.3 parts of diethyl (3-methoxycarbonylthienyl)aminomethylenemalonate in a mixture of 20 parts by volume of chloroform and 4 parts by volume of pyridine, 0.6 part by volume of bromide is added dropwise. The solution is further stirred at room temperature for 15 minutes, after which the reaction mixture is washed with dilute hydrochloric acid, an aqueous sodium hydrogen carbonate solution and water, followed by drying over $Na_2SO_4$. The solvent is distilled off to give diethyl (5-bromo-3-methoxycarbonylthienyl)aminomethylenemalonate. Recrystallization from ethanol gives light-yellowish needles melting at 129°–130°C.

Elemental analysis, $C_{14}H_{16}BrNO_6S$. Calcd: C, 41.39; H, 3.97; N, 3.45. Found: C, 41.31; H, 3.72; N, 3.15.

REFERENCE EXAMPLE 14

Under similar conditions to those set forth in Reference Example 11, diethyl (5-bromo-3-methoxycarbonylthienyl)aminomethylenemalonate is hydrolyzed to 2-(2,2-bis-ethoxycarbonyl)vinylamino-5-bromothiophene-3-carboxylic acid, melting point: 191°–193°C. This product is identical with the product obtained in Reference Example 12.

REFERENCE EXAMPLE 15

A mixture of 9.8 parts of diethyl (3-methoxycarbonylthienyl)aminomethylenemalonate, 7.8 parts of iodine, 7.4 parts of mercuric oxide and 120 parts by volume of chloroform is stirred vigorously at room temperature for 1 hour. The reaction mixture is filtered and the filtrate is washed with a 5 % aqueous solution of potassium iodide and, then, with water, followed by concentration.

The crystalline residue is recrystallized from methanol to give diethyl (5-iodo-3-methoxycarbonylthienyl)aminomethylenemalonate as yellow needles melting at 163°–164°C.

Elemental analysis, $C_{14}H_{16}INO_6S$. Calcd: C, 37.10; H, 3.56; N, 3.09. Found: C, 37.10; H, 3.37; N, 3.10.

Reference Example 16

Diethyl (5-iodo-3-methoxycarbonylthienyl)aminomethylenemalonate is hydrolyzed under similar conditions to those set forth in Reference Example 11, whereupon 2-(2,2-bisethoxycarbonyl)-vinylamino-5-iodothiophene-3-carboxylic acid is obtained as crystals, melting at 195°–197°C.

Elemental analysis, $C_{13}H_{14}INO_6S$. Calcd: C, 35.55; H, 3.21; N, 3.19. Found: C, 35.51; H, 3.07; N, 3.14.

REFERENCE EXAMPLE 17

To a stirred solution of 4 parts of methyl 2-acetamidothiophene-3-carboxylate in a mixture of 80 parts by volume of chloroform and 12 parts by volume of pyridine, 20 parts by volume of a 10 % (W/V) solution of chlorine in carbon tetrachloride is added dropwise. After stirring for further 30 minutes, the mixture is washed with an aqueous sodium bicarbonate solution and, then, with water. Evaporation of the solvent, and recrystallization of the residue from methanol gives methyl 2-acetamido-5-chlorothiophene-3-carboxylate as crystals. Colorless needles, melting point: 110°–110.5°C.

REFERENCE EXAMPLE 18

To a stirred solution of 19.9 parts of methyl 2-acetamidothiophene-3-carboxylate in 200 parts by volume of chloroform, 8.2 parts by volume of sulfuryl chloride is added dropwise at below 30°C. The mixture is stirred at room temperature for 30 minutes and then cooled with ice. To the mixture, about 300 parts by volume of saturated aqueous sodium bicarbonate solution is cautiously added with stirring. The chloroform layer is separated, washed with water and dried over sodium sulfate. Evaporation of the solvent gives methyl 2-acetamido-5-chlorothiophene-3-carboxylate as crystals. Recrystallization from methanol gives needles melting at 110°–110.5°C. This compound is identical with that obtained in Reference Example 17.

REFERENCE EXAMPLE 19

A mixture of 9.5 parts of methyl 2-acetamido-5-chlorothiophene-3-carboxylate, 400 parts by volume of methanol and 8 parts of methanesulfonic acid is refluxed for 3 hours and, then, concentrated.

To the concentrate is added an aqueous sodium bicarbonate solution and the resulting crystals are collected by filtration and washed with water. Recrystallization from isopropanol gives methyl 2-amino-5-chlorothiophene-3-carboxylate as colorless crystals melting at 99°–101°C.

REFERENCE EXAMPLE 20

A mixture of 14.2 parts of methyl 2-acetamido-5-chlorothiophene-3-carboxylate, 360 parts by volume of methanol and 30 parts by volume of boron trifluoride-etherate is refluxed for 4 hours. After evaporation of the solvent the residue is treated in a manner similar to that used in Reference Example 19, whereby methyl 2-amine-5-chlorothiophene-3-carboxylate is obtained as crystals melting at 100°–102.5°C. This product is identical with that obtained in Reference Example 19.

REFERENCE EXAMPLE 21

Reaction of methyl 2-amino-5-chlorothiophene-3-carboxylate with diethyl ethoxymethylenemalonate in a similar manner to that used in Reference Example 10 yields diethyl (5-chloro-3-methoxycarbonylthienyl)aminomethylenemalonage as crystals melting at 89.5°–90.5°C.

REFERENCE EXAMPLE 22

Hydrolysis of diethyl (5-chloro-3-methoxycarbonylthienyl)aminomethylenemalonate with 3N ethanolic solution of potassium hydroxide in a manner similar to that used in Reference Example 11 yields 2-(2,2-bisethoxycarbonyl)vinylamino-5-chlorothiophene-3-carboxylic acid as crystals melting at 184°–186°C.

REFERENCE EXAMPLE 23

Reaction of methyl 2-amino-4-methylthiophene-3-carboxylate with diethyl ethoxymethylenemalonate in a manner similar to that used in Reference Example 10 yields diethyl (3-methoxycarbonyl-4-methylthienyl)aminomethylenemalonate as crystals melting at 105.5°–106°C.

REFERENCE EXAMPLE 24

Hydrolysis of diethyl (3-methoxycarbonyl-4-methylthienyl)aminomethylenemalonate with 3N ethanolic solution of potassium hydroxide in a manner similar to that used in Reference Example 11 yields 2-(2,2-bisethoxycarbonyl)-4-methylthiophene-3-carboxylic acid as crystals melting at 180°–185°C.

REFERENCE EXAMPLE 25

Bromination of 2-(2,2-bisethoxycarbonyl)vinylamino-4-methylthiophene-3-carboxylic acid with bromine in a manner similar to that used in Reference Example 12 yields 5-Bromo-2-(2,2-bisethoxycarbonyl)vinylamino-4-methylthiophene-3-carboxylic acid as crystals melting at 188°–190°C.

EXAMPLE 1

A mixture of 10 parts of 2-(2,2-bisethoxycarbonyl)vinylamino-5-methylthiophene-3-carboxylic acid and 20 parts of diphenyl ether is heated at 190°–210°C for 40 minutes. After cooling, the reaction mixture is extracted with hot n-hexane and the extract is subjected to column chromatography on silica gel (90 parts). After washing the column with n-hexane to remove the diphenyl ether, the product is eluted with isopropyl ether. The isopropyl ether fraction is concentrated and the crystalline residue is collected and washed with h-hexane, whereupon ethyl 4-hydroxy-2-methyl-thieno[2,3-b]-pyridine-5-carboxylate is obtained as yellow prisms. Recrystallization from isopropyl ether yields yellow prisms melting at 122°–123°C.

Elemental analysis, $C_{11}H_{11}NO_3S$. Calcd: C, 55.68; H, 4.67; N, 5.90. Found: C, 55.49; H, 4.64; N, 5.89.

EXAMPLE 2

To stirred hot polyphosphate ester (98 parts), 9.8 parts of 2-(2,2-bisethoxycarbonyl)vinylamino-5-methylthiophene-3-carboxylic acid is added in portions at 150°C. After the addition, the mixture is further heated for 30 minutes with stirring. After cooling, 250 parts by volume of ice-water is added, followed by extraction with chloroform.

The chloroform extract is washed with water, dried over $Na_2SO_4$ and evaporated to remove the solvent. The residue is extracted with hot isopropyl ether and the extract is concentrated. The resultant crystals are recovered by filtration and washed with isopropyl ether and n-hexane. This procedure gives ethyl 4-hydroxy-2-methylthieno[2,3-b]pyridine-5-carboxylate as yellowish crystals melting at 118°–120°C. The infrared absorption spectrum of this product coincides with that of the compound acccording to Example 1.

EXAMPLE 3

To 60 parts of polyphosphate ester is added 5.67 parts of diethyl (5-methylthienyl)aminomethylenemalonate and the mixture is heated at 120°–125°C in a manner similar to that used in Example 2. Then, the product is similarly isolated to obtain light-yellowish crystals of ethyl 4-hydroxy-2-methylthieno[2,3-b]-pyridine-5-carboxylate, melting at 123°–125°C. The infrared absorption spectrum of this product is identical with that of the product according to Example 1 or 2.

EXAMPLE 4

A mixture of 1.9 parts of ethyl 4-hydroxy-2-methyl-thieno-[2,3-b]pyridine-5-carboxylate and 30 parts by volume of 10 % aqueous potassium hydroxide is heated on a boiling water bath for 30 minutes. After cooling, the reaction mixture is made acidic with acetic acid and the precipitate is collected by filtration, whereupon 4-hydroxy-2-methylthieno[2,3-b]pyridine-5-carboxylic acid is obtained as crystals. This product is purified by dissolving in an aqueous solution of sodium bicarbonate and then making acidic with acetic acid. The resulting crystals are collected by filtration, washed well with water and methanol, and then dried to yield colorless needlets melting at 243°–244°C (decomposition).

Elemental analysis, $C_9H_7NO_3S$. Calcd: C, 51.66; H. 3.37; N, 6.70. Found: C, 51.52; H 3.18; N, 6.70.

EXAMPLE 5

A mixture of 9.7 parts of diethyl (4,5,6,7-tetrahydrobenzo-[b]thienyl)aminomethylenemalonate and 97 parts of polyphosphate ester is heated at 130°C for 30 minutes and cooled. The reaction mixture is added to ice-water and the resulting precipitate is collected by filtration, washed with water and dried. This procedure gives ethyl 4-hydroxy-5,6,7,8-tetrahydro[1]benzothieno-[2,3-b]pyridine-3-carboxylate as crystals. Recrystallization from ethanol yields colorless needles melting at 141.5°–142°C.

Elemental analysis, $C_{14}H_{15}NO_3S$. Calcd: C, 60.63; H, 5.45; N, 5.04. Found: C, 60.66; H, 5.24; N, 5.08.

EXAMPLE 6

By a procedure similar to that described in Example 5, 0.74 part of 2-(2,2-bisethoxycarbonyl)vinylamino-4,5,6,7-tetrahydrobenzo-[b]thiophene-3-carboxylic acid is heated in 7.4 parts of polyphosphate ester at 120°–130°C. Similar treatment of the reaction mixture gives ethyl 4-hydroxy-5,6,7,8-tetrahydro[1]benzothieno-[2,3-b]pyridine-3-carboxylate as crystals melting at 138°–140°C. The infrared absorption spectrum of this product is identical with that of the compound according to Example 5.

EXAMPLE 7

When a mixture of 2-(2,2-bisethoxycarbonyl)-vinylamino-4,5,6,7-tetrahydrobenzo[b]thiopene-3-carbocylic acid and diphenyl ether is heated at 200°–220°C and the reaction mixture is treated by a procedure similar to that described in Example 1, ethyl 4-hydroxy-5,6,7,8-tetrahydro[1]benzothieno[2,3-b]pyridine-3-carboxylate is obtained as crystals melting at 138°–140°C. The infrared absorption spectrum of this product is identical with that of the compound according to Example 5 or 6.

EXAMPLE 8

A mixture of 0.28 part of ethyl 4-hydroxy-5,6,7,8-tetrahydro-[1]benzothieno[2,3-b]pyridine-3-carboxylate and 6 parts by volume of 10 % aqueous potassium hydroxide is heated at 100°C for 30 minutes, after which it is neutralized with hydrochloric acid. The resultant crystals are collected by filtration, washed with water and dried, whereupon 4-hydroxy-5,6,7,8-tetrahydro[1]benzothieno[2,3-b]pyridine-3-carboxylic acid is obtained as crystals. Recrystallization from chloroform-methanol gives colorless needles, melting point: 250°–252°C (decomposition).

EXAMPLE 9

By a procedure similar to that in Example 3, 17 parts of 2-(2,2-bisethoxycarbonyl)vinylamino-5-ethylthio-phene-3-carboxylic acid is heated with 170 parts of polyphosphate ester at 120°C, and the product is similarly isolated. The procedure gives ethyl 2-ethyl-4-hydroxythieno[2,3-b]pyridine-5-carboxylate as crystals. Recrystallization from ethanol yields yellow prisms melting at 121°–122°C.

EXAMPLE 10

Hydrolysis of ethyl 2-ethyl-4-hydroxythieno[2,3-b]pyridine-5-carboxylate under conditions similar to those used in EXAMPLE 4 gives 2-ethyl-4-hydroxy-thieno[2,3-b]pyridine-5-carboxylic acid as crystals melting at 238°–239°C.

EXAMPLE 11

To stirred 112 parts of hot polyphosphate ester is added portionwise, 5.6 parts of 2-(2,2-bisethoxycarbonyl)vinylamino-5-bromothiophene-3-carboxylic acid at 120°–130°C and the mixture is further heated for 30 minutes. After cooling, 300 parts by volume of ice-water is added and the mixture is extracted with chloroform. The chloroform layer is washed with water, dried over $Na_2SO_4$ and decolorized with active charcoal. Evaporation of the solvent gives ethyl 2-bromo-4-hydroxythieno[2,3-b]pyridine-5-carboxylate as crystals. The crystals are washed with ethanol and recrystallized from chloroform-ethanol to give yellowish fine crystals melting at 201°–203°C.

Elemental analysis, $C_{10}H_8BrNO_3S$. Calcd: C, 39.75; H, 2.67; N, 4.64. Found: C, 39.79; H, 2.43; N, 4.57.

EXAMPLE 12

A mixture of 15 parts by volume of 2N potassium hydroxide and 1.5 parts of ethyl 2-bromo-4-hydroxy-thieno[2,3-b]pyridine-5-carboxylate is heated at 90°–95°C for 40 minutes. After cooling, 30 parts by volume of methanol is added and the mixture is neutralized with acetic acid, whereupon 2-bromo-4-hydroxythieno[2,3-b]pyridine-5-carboxylic acid is obtained as crystals. The crystals are collected by filtration, and washed with water and recrystallized from an aqueous solution of potassium hydroxide-acetic acid. The procedure gives colorless needles, melting at 262°–263°C.

Elemental analysis: $C_8H_4BrNO_3S$. Calcd: C, 35.05; H, 1.47; N, 5.11. Found: C, 34.92; H, 1.23; N, 4.96.

EXAMPLE 13

A mixture of 1.4 parts of ethyl 4-hydroxy-2-methyl-thieno-[2,3-b]pyridine-5-carboxylate, 12 parts by volume of 10 % aqueous potassium hydroxide, 48 parts by volume of ethanol, 60 parts by volume of water and 1.8 parts by volume of ethyl iodide is refluxed for about 3 hours. After cooling, the reaction mixture is added to 60 parts by volume of water containing 3 parts by volume of concentrated hydrochloric acid and the resulting crystals are collected by filtration to give 7-ethyl-4,7-dihydro-2-methyl-4-oxothieno[2,3-b]pyridine-5-carboxylic acid as colorless crystals. Recrystallization from chloroform-ethanol yields colorless prisms melting at 229°–230°C.

Elemental analysis, $C_{11}H_{11}NO_3S$. Calcd: C, 55.68; H, 4.67; N, 5.90. Found: C, 55.66; H, 4.49; N, 5.63.

EXAMPLE 14

To a solution comprising 0.21 part of 4-hydroxy-2-methylthieno[2,3-b]pyridine-5-carboxylic acid and 5 parts by volume of a 4 % aqueous potassium hydroxide solution is added 0.24 part by volume of dimethyl sulfate. After stirring at room temperature overnight, the mixture is made acidic with acetic acid. The resulting precipitate is collected by filtration, whereupon 4,7-dihydro-2,7-dimethyl-4-oxothieno[2,3-b]pyridine-5-carboxylic acid is obtained as crystals. Recrystallization from chloroform-ethanol gives colorless needles, melting point: 288°–290°C.

Elemental analysis, $C_{10}H_9NO_3S$. Calcd: C, 53.80; H, 4.06; N, 6.27. Found: C, 53.62; H, 4.06; N, 6.61.

EXAMPLE 15

The procedure of Example 13 is followed except for using diethyl sulfate in place of dimethyl sulfate, whereby 7-ethyl-4,7-dihydro-2-methyl-4-oxothieno[2,3-b]pyridine-5-carboxylic acid is obtained. Recrystallization from chloroform-ethanol yields colorless granules melting at 229°–230°C. The compound is identical with the product prepared in Example 13.

EXAMPLE 16

The procedure of Example 13 is followed except for using propyl bromide in place of ethyl iodide to obtain 4,7-dihydro-2-methyl-4-oxo-7-propylthieno[2,3-b]pyridine-5-carboxylic acid. Recrystallization from chloroform-ethanol gives colorless plates melting at 207°–207.5°C.

EXAMPLE 17

The procedure of Example 13 is followed except for using n-butyl bromide in place of ethyl iodide to obtain 7-n-butyl-4,7-dihydro-2-methyl-4-oxothieno[2,3-b]pyridine-5-carboxylic acid. Recrystallization from methanol gives colorless plates melting at 172°–173°C.

EXAMPLE 18

A mixture of 1.38 parts of ethyl 4-hydroxy-5,6,7,8-tetrahydro[1]benzothieno[2,3-b]pyridine-3-carboxylate, 11 parts by volume of 10 % aqueous potassium hydroxide, 44 parts by volume of ethanol and 45 parts by volume of water and 1.5 parts by volume of ethyl iodide is refluxed for 4 hours and the product is isolated in a manner similar to that described in Example 13, whereby 1-ethyl-1,4,5,6,7,8-hexahydro-4-oxo[1]benzothieno[2,3-b]pyridine-3-carboxylic acid is obtained as crystals. Recrystallization from ethanol and, then, from tetrahydrofuran gives colorless needles melting at 218°–221°C.

Elemental analysis, $C_{14}H_{15}NO_3S$. Calcd: C, 60.63; H, 5.45; N, 5.04. Found: C, 60.40; H, 5.43; N, 4.90.

EXAMPLE 19

In a manner similar to that described in Example 13, ethyl 2-ethyl-4-hydroxythieno[2,3-b]pyridine-5-carboxylate is reacted with ethyl iodide to obtain 2,7-diethyl-4,7-dihydro-4-oxothieno-[2,3-b]pyridine-5-carboxylic acid. Recrystallization from methanol gives colorless prisms melting at 197°–198°C.

EXAMPLE 20

A mixture of 0.274 part of 2-bromo-4-hydroxythieno[2,3-b]-pyridine-5-carboxylic acid in 3 parts by volume of 2N potassium hydroxide and 0.4 part by volume of diethyl sulfate is stirred for 3 hours. Then, 1.5 parts by volume of 2N potassium hydroxide and 0.4 part by volume of diethyl sulfate are further added. Three hours later, another 1.5 parts by volume of 2N potassium hydroxide and 0.4 part by volume of diethyl sulfate are added. After stirring for 2 hours, the mixture is allowed to stand overnight, and then made acidic with acetic acid, whereupon 2-bromo-7-ethyl-4,7-dihydro-4-oxothieno[2,3-]pyridine-5-carboxylic acid is separated as crystals. The crystals are collected by filtration, washed with water and recrystallized from chloroform-ethanol. The procedure gives colorless plates melting at 239°–240°C.

Elemental analysis, $C_{10}H_8BrNO_3S$. Calcd: C, 39.75; H, 2.67; N, 4.64. Found: C, 39.81; H, 2.67; N, 4.53.

EXAMPLE 21

To a solution of 0.274 part of 2-bromo-4-hydroxythieno[2,3-b]pyridine-5-carboxylic acid in 3 parts by volume of a 2N aqueous solution of potassium hydroxide is added 0.24 part by volume of dimethyl sulfate. Treatment of the mixture in the manner described in Example 20 gives 2-bromo-4,7-dihydro-7-methyl-4-oxothieno[2,3-b]pyridine-5-carboxylic acid as crystals. Recrystallization from dimethylformamide-water gives colorless needles melting at 288°–290°C.

Elemental analysis, $C_9H_6BrNO_3S$. Calcd. C, 37.51; H, 2.10; N, 4.86. Found: C, 37.42; H, 1.87; N, 4.81.

EXAMPLE 22

A mixture of 0.274 part of 2-bromo-4-hydroxythieno[2,3-b]-pyridine-5-carboxylic acid, 0.250 part of n-propyl bromide, 2 parts by volume of 2N potassium hydroxide and 3 parts by volume of ethanol is refluxed for 2 hours. Another 0.250 part of n-propyl bromide is added thereto and the mixture is further refluxed for 3 hours. The ethanol is distilled off and the residue is made acidic with acetic acid, whereupon 2-bromo-4,7-dihydro-4-oxo-7-propylthieno-[2,3-b]pyridine-5-carboxylic acid is obtained as crystals. Recrystallization from chloroform-ethanol gives colorless plates melting at 208°–209°C.

Elemental analysis, $C_{11}H_{10}BrNO_3S$. Calcd: C, 41.78; H, 3.19; N, 4.43. Found: C, 41,62; H, 3.03; N, 4.51.

EXAMPLE 23

2-Bromo-4,7-dihydro-4-oxo-7-propylthieno[2,3-b]pyridine-5-carboxylic acid is also obtained as crystals melting at 208°–209°C by reacting 0.302 part of ethyl 2-bromo-4-hydroxythieno[2,3-b]pyridine-5-carboxylate with n-propyl bromide in the same manner as Example 22. This product is identical with the product obtained in Example 22.

EXAMPLE 24

A suspension of 0.237 part of 7-ethyl-4,7-dihydro-2-methyl-4-oxothieno[2,3-b]pyridine-5-carboxylic acid and 0.83 part of pulverized potassium carbonate in 6 parts by volume of dry dimethylformmide is stirred under heating at 100°C for 1 hour. To the mixture is then added 0.3 part by volume of diethyl sulfate. The mixture is stirred under heating at 100°C for 1 hour and filtered to remove insoluble material. The filtrate is concentrated to dryness under reduced pressure and the residue is extracted with chloroform. Evaporation of the solvent from the extract gives ethyl 7-ethyl-4,7-dihydro-2-methyl-4-oxothieno[2,3-b]pyridine-5-carboxylate as crystals. Recrystallization from ethyl acetate yields colorless plates melting at 140°–142°C.

Elemental analysis $C_{13}H_{15}NO_3S$. Calcd: C, 58.84; H, 5.69; N, 5.27. Found: C, 58.78; H, 5.80; N, 5.08.

EXAMPLE 25

A mixture of 0.237 part of ethyl 2-methyl-4-hydroxythieno-[2,3-b]pyridine-5-carboxylate, 5 parts by volume of dry dimethyl-formamide and 0.048 part of 50 % sodium hydride in mineral oil is heated at 70°C for 30 minutes, and 0.12 part by volume of ethyl iodide is added thereto. The mixture is heated at 70°C for 2 hours and the solvent is evaporated under reduced pressure. The residue is extracted with chloroform, and the extract is washed with saturated aqueous sodium chloride and dried over sodium sulfate. Evaporation of the solvent gives ethyl 7-ethyl-4,7-dihydro-2-methyl-4-oxothieno[2,3-b]pyridine-5-carboxylate as crystals. Recrystallization from ethyl acetate yields colorless plates melting at 140°–142°C. This product is identical with the product in Example 24.

EXAMPLE 26

A mixture of 0.24 part of ethyl 7-ethyl-4,7-dihydro-2-methyl-4-oxothieno[2,3-b]pyridine-5-carboxylate and 3 parts by volume of 2N sodium hydroxide is heated at 90°C for 5 minutes. After cooling the solution is neutralized with acetic acid to give a precipitate whic is collected by filtration, whereby 7-ethyl-4,7-dihydro-2-methyl-4-oxothieno[2,3-b]pyridine-5-carboxylic acid is obtained as crystals. Recrystallization from chloroform-ethanol gives colorless prisms melting at 232°–233°C. This product is identical with the product in Example 13.

According to procedures analogous to those described in the above Examples 1–26, the following compounds are prepared:

Ethyl 4-hydroxy-2,3-dimethylthieno[2,3-b]pyridine-5-carboxylate; melting point 176°–178°C (recrystallized from ethanol)

7-Ethyl-4,7-dihydro-2,3-dimethyl-4-oxothieno[2,3-b]pyridine-5-carboxylic acid; melting point 265°–266°C (recrystallized from chloroform-methanol).

Ethyl 4-hydroxythieno[2,3-b]pyridine-5-carboxylate; melting point 137°–139°C (recrsyallized from methanol)

4-Hydroxythieno[2,3-b]pyridine-5-carboxylic acid; melting point 237°–238°C (decomposition) (recrystallized from dimethyl-formamide-water).

7-Ethyl-4,7-dihydro-4-oxothieno[2,3-b]pyridine-5-carboxylic acid; melting point 264°–265°C (recrystallized from chloroform-methanol).

Ethyl 4-hydroxy-3-methylthieno[2,3-b]pyridine-5-carboxylate; melting point 186°–188°C (recrystallized from chloroform-ethanol).

4-Hydroxy-3-methylthieno[2,3-b]pyridine-5-carboxylic acid; melting point 252°–253°C (decomposition) (recrystallized from methanolic potassium hydroxide-acetic acid).

7-Ethyl-4,7-dihydro-3-methyl-4-oxothieno[2,3-b]pyridine-5-carboxylic acid; melting point 186°–188°C (recrystallized from chloroform-ethanol).

Ethyl 4-hydroxy-2-iodothieno[2,3-b]pyridine-5-carboxylate; melting point 210°–212°C (recrystallized from chloroform-ethyl acetate).

4-Hydroxy-2-iodothieno[2,3-b]pyridine-5-carboxylic acid; melting point 249°–250°C (recrystallized from methanolic potassium hydroxide-acetic acid).

7-Ethyl-4,7-dihydro-2-iodo-4-oxothieno[2,3-b]pyridine-5-carboxylic acid; melting point 243°–245°C (recrystallized from chloroform-methanol).

Ethyl 2-chloro-4-hydroxythieno[2,3-b]pyridine-5-carboxylate; melting point 188°–190°C (recrystallized from chloroform-ethanol)

2-Chloro-4-hydroxythieno[2,3-b]pyridine-5-carboxylic acid; melting point 255°–256°C (recrystallized from methanolic potassium hydroxide-acetic acid)

2-Chloro-4,7-dihydro-7-methyl-4-oxothieno[2,3-b]pyridine-5-carboxylic acid; melting point 264°–266°C (recrystallized from dichloromethane-methanol)

2-Chloro-7-ethyl-4,7-dihydro-4-oxothieno[2,3-b]pyridine-5-carboxylic acid; melting point 244°–245°C (recrystallized from chloroform-ethanol).

Ethyl 2-bromo-4-hydroxy-3-methylthieno[2,3-b]pyridine-5-carboxylate; melting point 206°–208°C (recrystallized from chloroform-ethanol).

2-Bromo-4-hydroxy-3-methylthieno[2,3-b]pyridine-5-carboxylic acid; melting point 253°–254°C (decomposition) (recrystallized from methanolic potassium hydroxide-acetic acid)

2-Bromo-7-ethyl-4,7-dihydro-3-methyl-4-oxothieno[2,3-b]-pyridine-5-carboxylic acid; melting point 245°–246°C (recrystallized from chloroform-ethanol)

Ethyl 2-bromo-7-ethyl-4,7-dihydro-4-oxothieno[2,3-b]pyridine-5-carboxylate; melting point 153°–156°C (recersytallized from ethyl acetate).

What we claim is:

1. A compound of the general formula

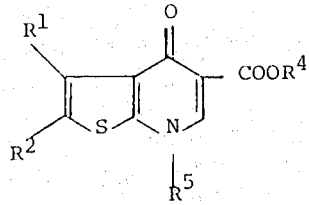

wherein $R^1$ represents hydrogen or a lower alkyl; $R^2$ represents hyrogen, a lower alkyl or a halogen; $R^4$ represents hydrogen or a lower alkyl, and $R^5$ represents a lower alkyl; or their pharmaceutically acceptable salts obtainable when $R^4$ is hydrogen.

2. A compound as claimed in claim 1, wherein $R^1$ is hydrogen.

3. A compound as claimed in claim 1, wherein $R^1$ is a lower alkyl.

4. A compound as claimed in claim 1, wherein R² is hyrogen.

5. A compound as claimed in claim 1, wherein R² is a lower alkyl.

6. A compound as claimed in claim 1, wherein R² is halogen.

7. A compound as claimed in claim 1, wherein R² is chlorine.

8. A compound as claimed in claim 1, wherein R² is bromine.

9. A compound as claimed in claim 1, wherein R² is iodine.

10. A compound as claimed in claim 1, wherein R⁴ is hydrogen.

11. A compound as claimed in claim 1, wherein R¹ and R⁴ are hydrogen.

12. A compound as claimed in claim 1, wherein R⁴ is a loweralkyl.

13. A compound as claimed in claim 1, wherein the compound is 4,7-dihydro-2,7-dimethyl-4-oxothieno[2,3-b]pyridine-5-carboxylic acid.

14. A compound as claimed in claim 1, wherein the compound is 7-ethyl-4,7-dihydro-2-methyl-4-oxothieno[2,3-b]pyridine-5-carboxylic acid.

15. A compound as claimed in claim 1, wherein the compound is ethyl 7-ethyl-4,7-dihydro-2-methyl-4-oxothieno[2,3-b]pyridine-5-carboxylate.

16. A compound as claimed in claim 1, wherein the compound is 4,7-dihydro-2-methyl-4-oxo-7-propylthieno[2,3-b]pyridine-5-carboxylic acid.

17. A compound as claimed in claim 1, wherein the compound is 7-n-butyl-4,7-dihydro-2-methyl-4-oxothieno[2,3-b]pyridine-5-carboxylic acid.

18. A compound as claimed in claim 1, wherein the compound is 2,7-diethyl-4,7-dihydro-4-oxothieno[2,3-b]pyridine-5-carboxylic acid.

19. A compound as claimed in claim 1, wherein the compound is 7-ethyl-4,7-dihydro-2,3-dimethyl-4-oxothieno[2,3-b]pyridine-5-carboxylic acid.

20. A compound as claimed in claim 1, wherein the compound is 7-ethyl-4,7-dihydro-4-oxothieno[2,3-b]pyridine-5-carboxylic acid.

21. A compound as claimed in claim 1, wherein the compound is 7-ethyl-4,7-dihydro-3-methyl-4-oxothieno[2,3-b]pyridine-5-carboxylic acid.

22. A compound as claimed in claim 1, wherein the compound is 2-bromo-4,7-dihydro-7-methyl-4-oxothieno[2,3-b]pyridine-5-carboxylic acid.

23. A compound as claimed in claim 1, wherein the compound is 2-bromo-7-ethyl-4,7-dihydro-4-oxothieno[2,3-b]pyridine-5-carboxylic acid.

24. A compound as claimed in claim 1, wherein the compound is ethyl 2-bromo-7-ethyl-4,7-dihydro-4-oxothieno[2,3-b]pyridine-5-carboxylate.

25. A compound as claimed in claim 1, wherein the compound is 2-bromo-4,7-dihydro-4-oxo-7-propylthieno[2,3-b]pyridine-5-carboxylic acid.

26. A compound as claimed in claim 1, wherein the compound is 7-ethyl-4,7-dihydro-2-iodo-4-oxothieno[2,3-pyridine-5-carboxylic acid.

27. A compound as claimed in claim 1, wherein the compound is 2-chloro-4,7-dihydro-7-methyl-4-oxothieno[2,3-b]pyridine-5-carboxylic acid.

28. A compound as claimed in claim 1, wherein the compound is 2-chloro-7-ethyl-4,7-dihydro-4-oxothieno[2,3-b]pyridine-5-carboxylic acid.

29. A compound as claimed in claim 1, wherein the compound is 2-bromo-7-ethyl-4,7-dihydro-3-methyl-4-oxothieno[2,3-b]pyridine-5-carboxylic acid.

* * * * *